(12) United States Patent
Chen et al.

(10) Patent No.: US 11,339,158 B2
(45) Date of Patent: May 24, 2022

(54) CRYSTALLINE FORM OF VALBENAZINE DITOSYLATE, PROCESSES FOR PREPARATION THEREOF AND USE THEREOF

(71) Applicant: Crystal Pharmaceutical (Suzhou) Co., Ltd., Jiangsu (CN)

(72) Inventors: Minhua Chen, Suzhou (CN); Yanfeng Zhang, Suzhou (CN); Chaohui Yang, Suzhou (CN); Chunxiang Huang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 62 days.

(21) Appl. No.: 16/771,799

(22) PCT Filed: Dec. 26, 2018

(86) PCT No.: PCT/CN2018/124039
§ 371 (c)(1),
(2) Date: Jun. 11, 2020

(87) PCT Pub. No.: WO2019/129100
PCT Pub. Date: Jul. 4, 2019

(65) Prior Publication Data
US 2021/0078993 A1  Mar. 18, 2021

(30) Foreign Application Priority Data
Dec. 26, 2017 (CN) .......................... 201711436859.7

(51) Int. Cl.
*C07D 471/04* (2006.01)
(52) U.S. Cl.
CPC ........ *C07D 471/04* (2013.01); *C07B 2200/13* (2013.01)
(58) Field of Classification Search
CPC .................................................. C07D 471/04

USPC ........................................................ 514/294
See application file for complete search history.

(56) References Cited

FOREIGN PATENT DOCUMENTS

| CN | 109528665 A | | 3/2019 |
|---|---|---|---|
| WO | 2008/058261 A1 | | 5/2008 |
| WO | 2015/120317 A1 | | 8/2015 |
| WO | 2015/171802 A1 | | 11/2015 |
| WO | 2016/210180 A2 | | 12/2016 |
| WO | 2017/075340 | * | 5/2017 |
| WO | 2017/075340 A1 | | 5/2017 |
| WO | 2017/112857 A1 | | 6/2017 |
| WO | 2018/067945 | * | 4/2018 |
| WO | 2018/067945 A1 | | 4/2018 |
| WO | 2018/102673 A1 | | 6/2018 |
| WO | 2018/140092 A1 | | 8/2018 |
| WO | 2018/140093 A1 | | 8/2018 |
| WO | 2018/140094 A1 | | 8/2018 |
| WO | 2018/140095 A2 | | 8/2018 |
| WO | 2018/140096 A1 | | 8/2018 |
| WO | 2018/153632 | * | 8/2018 |
| WO | 2018/153632 A1 | | 8/2018 |
| WO | 2018/164996 A1 | | 9/2018 |
| WO | 2018/200605 A1 | | 11/2018 |
| WO | 2019/060322 A2 | | 3/2019 |
| WO | 2019/074492 A1 | | 4/2019 |
| WO | 2019/104141 A1 | | 5/2019 |

OTHER PUBLICATIONS

International Search Report and Written Opinion for Application No. PCT/CN2018/124039, dated Mar. 28, 2019, 11 pages.

* cited by examiner

*Primary Examiner* — Niloofar Rahmani
(74) *Attorney, Agent, or Firm* — McCarter & English, LLP; Steven G. Davis; Wei Song (57) ABSTRACT

A crystalline form of valbenazine ditosylate, processes for preparation thereof, a pharmaceutical composition containing the crystalline form, use of the crystalline form for preparing vesicular monoamine transporter 2 inhibitor drugs, and use of the crystalline form for preparing drugs treating tardive dyskinesia.

7 Claims, 6 Drawing Sheets

CRYSTALLINE FORM OF VALBENAZINE DITOSYLATE, PROCESSES FOR PREPARATION THEREOF AND USE THEREOF

CROSS-REFERENCE TO RELATED APPLICATIONS

This application is a U.S. national stage filing, under 35 U.S.C. § 371(c), of International Application No. PCT/CN2018/124039, filed on Dec. 26, 2018, which claims priority to Chinese Patent Application No. 201711436859.7, filed on Dec. 26, 2017. The entire contents of each of the aforementioned applications are incorporated herein by reference.

The present disclosure relates to the field of pharmaceutical chemistry, particularly relates to crystalline forms of valbenazine ditosylate, processes for preparation and use thereof.

BACKGROUND

Tardive dyskinesia (TD) is a neurological condition characterized by involuntary movements of the orofacial region (i.e., tongue, lips, jaw and face) and choreoathetoid movements in the limbs and trunk. Patients with mild TD are typically unaware of the involuntary movements and they do not seek treatment. As symptom severity increases, the hyperkinetic movements begin to disrupt normal speech, chewing, breathing, facial expression, limb movements, walking and balance. In the most severe cases, TD may result in self-injury, abrasions, lacerations, inability to dress, eat, or drink.

Dysregulation of dopaminergic systems is integral to several central nervous system disorders, including hyperkinetic movement disorders (e.g., tardive dyskinesia (TD)) schizophrenia, and bipolar disorder. The transporter protein vesicular monoamine transporter 2 (VMAT2) plays an important role in presynaptic dopamine release, regulating monoamine uptake from the cytoplasm to the synaptic vesicle for storage and release. Vesicular monoamine transporter 2 (VMAT2) inhibitors have been shown to be effective in treatment of various movement disorders (including tardive dyskinesia).

Valbenazine was developed by Neurocrine Biosciences, Inc. and targeted at VMAT2. Valbenazine was approved by the FDA for the treatment of adult patients with tardive dyskinesia on Apr. 11, 2017, and is marketed as a ditosylate. This is the first drug approved by the FDA for the treatment of tardive dyskinesia and it was granted fast track designation of approval application, priority review designation and breakthrough therapy designation by the FDA.

The chemical name of valbenazine is (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester (hereinafter referred to as "compound I"), and the structure is shown as follows:

Compound I

A crystalline form is a solid material whose constituents are arranged in a highly ordered microscopic structure, forming a crystal lattice. Polymorphism is the ability of a solid to exist in more than one crystalline form. Different crystalline forms have different physicochemical properties and can affect drug's in vivo dissolution and absorption, which will further affect drug's clinical efficacy and safety to some extent. Especially for poorly soluble drugs, the above effects of the crystalline form will be greater. Therefore, drug polymorphism is inevitably an important part of drug research and an important part of drug quality control.

WO2017075340A1 disclosed six crystalline forms of valbenazine ditosylate, namely Form I, Form II, Form III, Form IV, Form V and Form VI. The stability data of Form I was disclosed in detail in WO2017075340A1, and it clearly pointed out that the stability of Form I is much better than that of Form II and Form IV The hygroscopicity of form I is also better than that of other crystalline forms. In addition, example 17 of WO2017075340A1 disclosed that when valbenazine ditosylate was added into 24 different organic solvents for incubation, Form I was obtained in more than half of the experiments. In the rest experiments, amorphous, unknown forms or even no crystal was obtained. Thus, Form I is the most superior crystalline form among crystalline forms disclosed in WO2017075340A1.

However, the inventors of the present disclosure have found that there is a large loss of the API to obtain prior art Form I, and the yield is low. As disclosed in WO2017075340A1 example 2, the yield of Form I is only 69%. In addition, it is found that Form I has disadvantages in solubility, hygroscopicity and powder properties.

In order to overcome the disadvantages of prior art, the inventors of the present disclosure surprisingly discovered crystalline form A of compound I ditosylate, which has advantages in physiochemical properties, formulation processability and bioavailability, for example, crystalline form A of the present disclosure has advantages in at least one aspect of melting point, solubility, hygroscopicity, purification ability, stability, adhesiveness, compressibility, flowability, in vitro and in vivo dissolution, and bioavailability. Crystalline form A of the present disclosure has advantages in physicochemical stability, solubility, hygroscopicity, flowability, compressibility, and the yield of the crystalline form A is obviously higher than that of the Form I, when both crystalline forms was obtained from the same starting material, which provides a new and better choice for the development of valbenazine and is of great significance.

SUMMARY

The main objective of the present disclosure is to provide novel crystalline forms of valbenazine ditosylate, processes for preparation and use thereof.

According to the objective of the present disclosure, crystalline form A of compound I ditosylate is provided (hereinafter referred to as Form A).

According to one aspect of the present disclosure, the X-ray powder diffraction pattern of Form A shows characteristic peaks at 2theta values of 5.9°±0.2°, 13.3°±0.2° and 19.8°±0.2° using CuKα radiation.

Furthermore, the X-ray powder diffraction pattern of Form A shows one or two or three characteristic peaks at 2theta values of 11.0°±0.2°, 8.7°±0.2° and 15.8°±0.2°. Preferably, the X-ray powder diffraction pattern of Form A shows characteristic peaks at 2theta values of 11.0°±0.2°, 8.7°±0.2° and 15.8°±0.2°.

According to another aspect of the present disclosure, the X-ray powder diffraction pattern of Form A shows three or four or five or six characteristic peaks at 2theta values of 5.9°±0.2°, 13.3°±0.2°, 19.8°±0.2°, 11.0°±0.2°, 8.7°±0.2° and 15.8°±0.2° using CuKα radiation.

Figure 3:
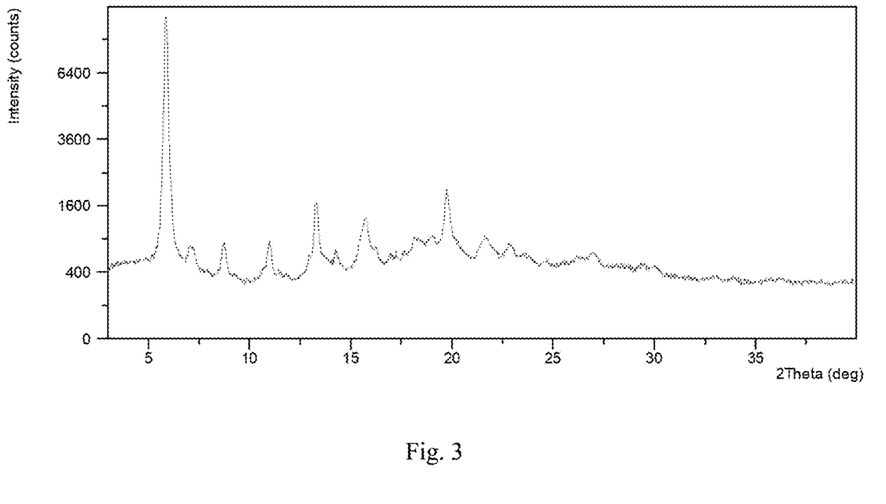
FIG. 3 shows an XRPD pattern of Form A

Without any limitation being implied, in a specific embodiment, Form A is a hydrate, and the X-ray powder diffraction pattern of Form A is substantially as depicted in FIG. 3.

Figure 7:
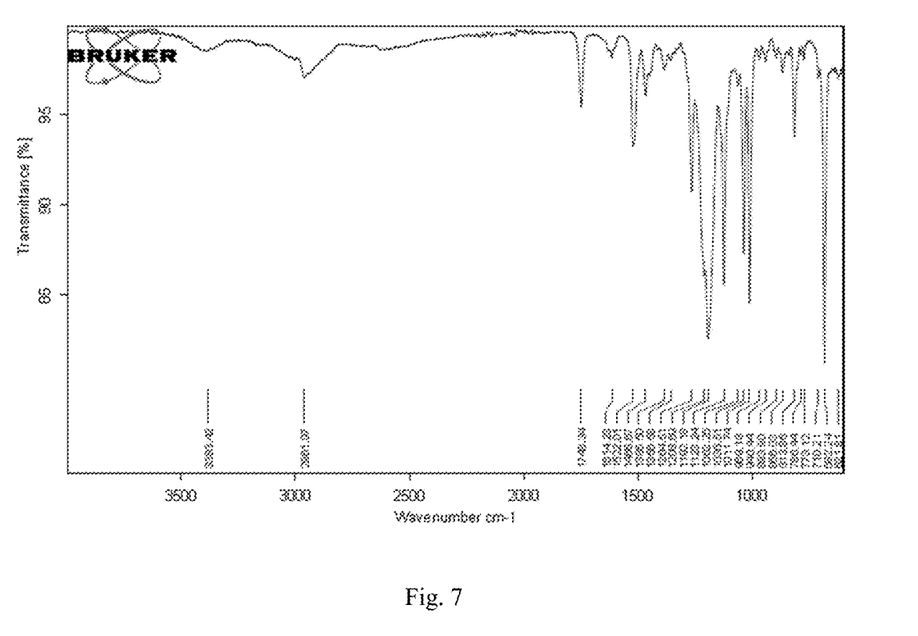
FIG. 7 shows an IR spectrum of Form A

The infrared spectrum of Form A is substantially as depicted in FIG. 7, having the following absorption bands: 621.81 cm$^{-1}$ (w), 682.24 cm$^{-1}$ (s), 710.21 cm$^{-1}$ (w), 773.12 cm$^{-1}$ (w), 786.44 cm$^{-1}$ (m), 813.86 cm$^{-1}$ (w), 866.03 cm$^{-1}$ (w), 893.90 cm$^{-1}$ (w), 940.44 cm$^{-1}$ (w), 969.18 cm$^{-1}$ (w), 1011.74 cm$^{-1}$ (s), 1036.51 cm$^{-1}$ (s), 1062.25 cm$^{-1}$ (w), 1123.24 cm$^{-1}$ (s), 1192.18 cm$^{-1}$ (s), 1208.69 cm$^{-1}$ (s), 1264.51 cm$^{-1}$ (m), 1356.58 cm$^{-1}$ (w), 1385.50 cm$^{-1}$ (w), 1466.67 cm$^{-1}$ (w), 1522.01 cm$^{-1}$ (m), 1614.23 cm$^{-1}$ (w), 1748.34 cm$^{-1}$ (m)(±2 cm$^{-1}$).

According to the objective of the present disclosure, a process for preparing Form A is also provided. The process comprises:

Adding a compound I ditosylate solvate into an ether, stirring, filtering the solid, and drying to obtain the crystalline form A.

In the process for preparing Form A:

Said solvate is preferably a 2-MeTHF and water co-solvate.

Figure 1:
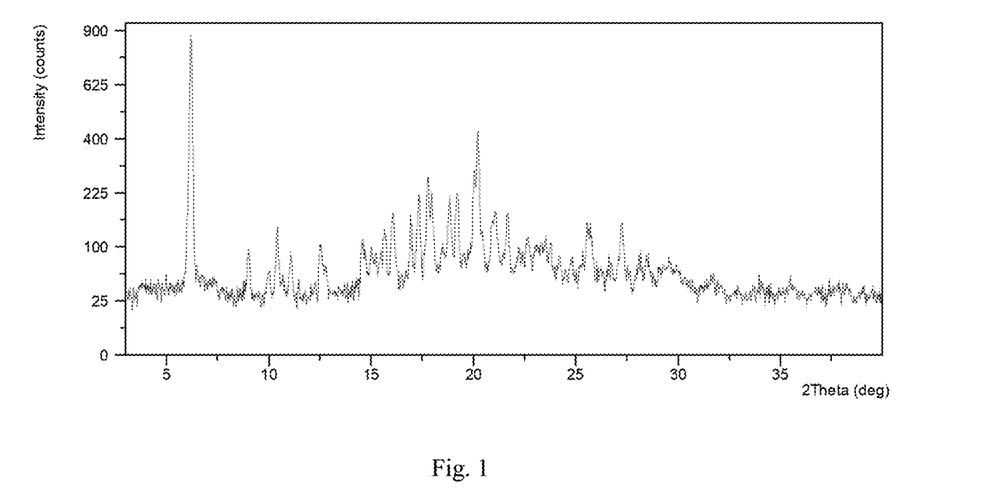
FIG. 1 shows an XRPD pattern of Form CSIII

In a specific embodiment, said solvate is Compound I ditosylate co-solvate crystalline form III (hereinafter referred to as Form III), its X-ray powder diffraction pattern is substantially as depicted in FIG. 1.

Said ether is preferably anisole.

Said stirring temperature is preferably 4° C.

Figure 2:
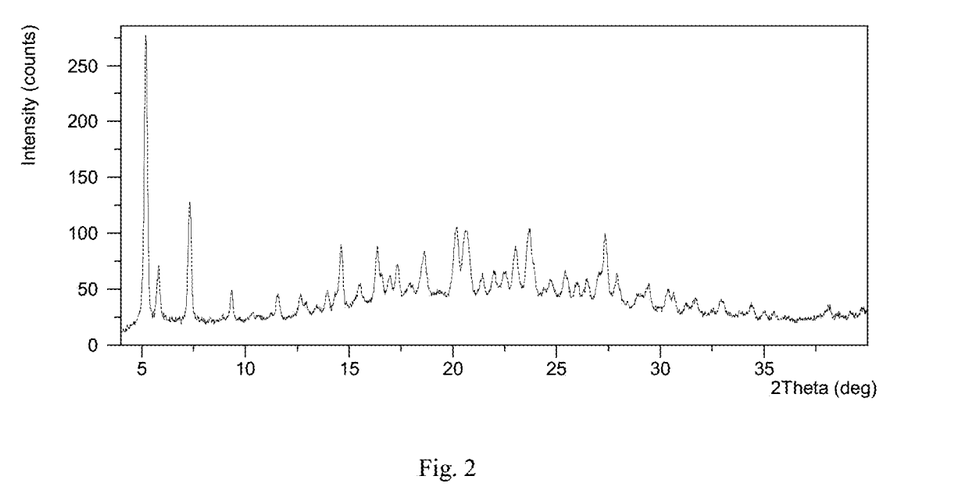
FIG. 2 shows an XRPD pattern of Form N4

Said solid obtained by filtering is a crystalline form (hereinafter referred to as Form N4), and its X-ray powder diffraction pattern is substantially as depicted in FIG. 2.

Form A of the present disclosure has the following advantages:

(1) Compared with prior art, Form A of the present disclosure is obtained in higher yield. According to prior art WO2017075340A1 example 2, the yield of Form I crude product obtained from free base is 69%. In example 3, the recrystallization process was further carried out, and the yield is 72%-88%. That is to say, the yield of final product of Form I obtained from free base is only 50%-61%. However, the yield of the final product of Form A of the present disclosure obtained from free base can reach 84%, which is increased by 23%-34% compared with the yield of prior art. Increasing the yield of drug preparation can greatly reduce the cost of production and has strong social and economic benefits.

(2) Compared with prior art, Form A of the present disclosure has higher solubility. In particularly in FeSSIF (Fed state simulated intestinal fluids), the solubility of Form A is 1.23 times higher than that of prior art Form I of WO 2017075340A1.

FaSSIF (Fasted state simulated intestinal fluids) and FeSSIF (Fed state simulated intestinal fluids) are biorelevant media, which can better reflect the effects of gastrointestinal environment on drug release. Solubility in such media is close to in vivo solubility. High solubility in biorelevant media is beneficial to improve drug's in vivo absorption and bioavailability, thus improving drug efficacy. In addition, drug dose reduction without affecting efficacy is possible due to higher solubility, thereby reducing the drug's side effects and improving drug safety.

(3) Compared with prior art, Form A of the present disclosure has lower hygroscopicity. Drug hygroscopicity test guideline in Chinese Pharmacopoeia was used for hygroscopicity test. The test results show that the hygroscopicity of Form A of the present disclosure is only 3/5 of that of prior art form. The weight gain of Form A is about 0.24%, while the weight gain of prior art Form I is as high as 0.40%, which is obviously higher than that of Form A of the present disclosure.

Hygroscopicity affects the physicochemical stability of the drug directly, as high hygroscopicity tends to cause chemical degradation and crystal transformation. In addition, high hygroscopicity will reduce the flowability of the drug, thereby affecting the processing of the drug. Moreover, drug substances with high hygroscopicity require low humidity environment during production and storage, which puts a strict requirement on production and imposes higher costs. More importantly, high hygroscopicity is likely to cause variation in the content of active pharmaceutical ingredients in the drug, thus affecting drug quality. The crystalline form with low hygroscopicity is not demanding on the environment, which reduces the cost of production, storage and quality control, and has strong economic value.

(4) Form A of the present disclosure has good purification effect. The purity is significantly increased after the free base raw material is converted into the crystalline form of the present disclosure. In a specific embodiment, the purity of the raw material used in the present disclosure is 99.09%. The purity of Form A obtained from the raw material is 99.38%, and the purity is increased by 0.29%. More importantly, after the raw material is made into Form A, the number of impurities detected is significantly reduced from the original 8 impurities to 5 impurities.

Chemical purity is of great significance for ensuring drug efficacy, safety and preventing the occurrence of adverse effects. If the drug contains impurities higher than limit, its physicochemical properties and drug appearance may change, and the stability will be affected. The increase in impurities will lead to significantly lowered active ingredient content or reduced drug activity, and will also lead to significantly increased toxicity and side effects of the drug products. Therefore, different drug regulations have strict requirements on impurity content. Crystalline forms with good purification effect are excellent in removing impurities in the crystallization process, thus drug substances with high purity can be obtained through crystallization, which effectively overcome the disadvantages of poor stability, poor efficacy and high toxicity caused by the low purity drug substances.

(5) Form A drug substance of the present disclosure is very stable and it also has good stability in drug product. The crystalline form and chemical purity of Form A drug substance doesn't change for at least 3 months in closed dish when stored under the condition of 25° C./60% RH. The crystalline form of Form A drug substance doesn't change for at least 3 months in open dish when stored under the condition of 25° C./60% RH. The chemical purity is only reduced by 0.03% and remains substantially unchanged during storage. After Form A is mixed with the excipients to form a drug product, the crystalline form doesn't change. When stored under the condition of 25° C./60% RH, the crystalline form of Form A in drug product doesn't change for at least 3 months. These results show that Form A drug substance and drug product are very stable and conducive to drug storage.

Meanwhile, the crystalline form of Form A drug substance doesn't change for at least 3 months when stored under the condition of 40° C./75% RH. The chemical purity is only reduced by 0.09% and remains substantially unchanged during storage. The crystalline form of Form A drug substance doesn't change for at least 1 week when stored under the condition of 60° C./75% RH. The chemical purity is only reduced by 0.08% and remains substantially unchanged during storage. Form A is mixed with the excipients to form a drug product. The crystalline form of Form A drug product doesn't change for at least 3 months when stored under the condition of 40° C./75% RH. These results show that Form A drug substance and drug product have good stability under accelerated and stress conditions. Good stability under accelerated and stress conditions is of great importance to the drug development. Drug substance and drug product will go through high temperature and high humidity conditions caused by weather, season and regional climate differences during storage, transportation, and manufacturing processes. Form A drug substance and drug product have good stability under these stress conditions, which is beneficial to avoid the influence on drug quality when not stored in condition recommended in label.

Meanwhile, Form A has good mechanical stability. The crystalline form of Form A drug substance doesn't change after tableting under 15 kN pressure and has good physical stability, which is beneficial to keep crystalline form unchanged during dry granulation and tableting process.

Crystal transformation can lead to changes in the absorption of the drug, affect bioavailability, and even cause toxicity and side effects. Good chemical stability ensures that no impurities are generated during storage. Form A has good physicochemical stability, ensuring consistent and controllable quality of the drug substance and drug product, minimizing change in quality, bioavailability due to crystal transformation or impurity generation.

(6) Compared with prior art, Form A has better in vitro dissolution and dissolution rate. In 0.1N HCl medium, the dissolution of Form A drug product at 30 minutes is up to 89.7%, meeting the requirements of rapid dissolution.

Drug with different crystalline forms may lead to different in vivo dissolution rates, which directly affects drug's in vivo absorption, distribution, excretion and metabolism, and finally leads to difference in clinical efficacy due to different bioavailability. Dissolution and dissolution rates are important prerequisites for drug absorption. Good in vitro dissolution leads to higher in vivo absorption, better in vivo exposure, thereby improving drug's bioavailability and efficacy. High dissolution rate is beneficial for the drug to achieve peak concentration in plasma quickly after administration, thus ensuring rapid drug action.

Furthermore, Form A of the present disclosure also has the following advantages:

(1) Compared with prior art, Form A of the present disclosure has better compressibility. Failure in hardness/friability test and tablet crack issue can be avoided due to better compressibility, making the preparation process more reliable, improving product appearance and product quality. Better compressibility can increase the compression rate, thus further increases the efficiency of process and reduces the cost of compressibility improving excipients.

(2) Compared with prior art, Form A of the present disclosure has better flowability. Flowability evaluation results indicate that the flowability of Form A is remarkably better than that of prior art forms. Better flowability can prevent clogging of production equipment and increase manufacturing efficiency. Better flowability of Form A ensures the blend uniformity and content uniformity of the drug product, and reduces the weight variation of the drug product and improves product quality.

(3) Compared with prior art, Form A of the present disclosure shows superior adhesiveness. Adhesiveness evaluation results indicate that adhesion quantity of Form A is remarkably lower than that of prior art form. Due to superior adhesiveness of Form A, adhesion to roller and tooling during dry-granulation and compression process can be reduced, which is also beneficial to improve product appearance and weight variation. In addition, superior adhesiveness of Form A can reduce the agglomeration of drug substance, which is beneficial to the dispersion of drug substance and reduce the adhesion between drug substance and other instruments, and improve the blend uniformity and content uniformity of drug product.

According to the objective of the present disclosure, a pharmaceutical composition is also provided. Said pharmaceutical composition comprises a therapeutically effective amount of Form A and pharmaceutically acceptable carriers, diluents or excipients.

Furthermore, Form A of the present disclosure can be used for preparing drugs inhibiting vesicular monoamine transporter 2.

Furthermore, Form A of the present disclosure can be used for preparing drugs treating tardive dyskinesia.

In the present disclosure, said "stirring" is accomplished by using a conventional method in the field such as magnetic stirring or mechanical stirring and the stirring speed is 50 to 1800 r/min, preferably the magnetic stirring speed is 300 to 900 r/min and mechanical stirring speed is 100 to 300 r/min.

Said "drying" is accomplished at room temperature or a higher temperature. The drying temperature is from room temperature to about 60° C., or to 50° C., or to 40° C. The drying time can be 2 to 48 hours, or overnight. Drying is accomplished in a fume hood, forced air convection oven or vacuum oven.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the preparation of sample and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, crystalline Form A of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

In the present disclosure, the term "about" when referring to a measurable value such as weight of a compound or formulation, time, temperature, and the like, is meant to encompass variations of ±10%, ±5%, ±1%, ±0.5%, or even±0.1% of the specified amount.

DETAILED DESCRIPTION

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:
XRPD: X-ray Powder Diffraction
DSC: Differential Scanning Calorimetry
TGA: Thermo Gravimetric Analysis
IR: Infrared
Instruments and methods used for data collection:
X-ray powder diffraction patterns in the present disclosure were acquired by a Bruker D2 PHASER X-ray powder diffractometer. The parameters of the X-ray powder diffraction method of the present disclosure are as follows:
X-ray Reflection: Cu, Kα
Kα1 (Å): 1.54060; Kα2 (Å): 1.54439
Kα2/Kα1 intensity ratio: 0.50
Voltage: 30 (kV)
Current: 10 (mA)
Scan range: from 3.0 degree to 40.0 degree
Differential scanning calorimetry (DSC) data in the present disclosure were acquired by a TA Q2000. The parameters of the DSC method of the present disclosure are as follows:
Heating rate: 10° C./min
Purge gas: nitrogen
Thermal gravimetric analysis (TGA) data in the present disclosure were acquired by a TA Q500. The parameters of the TGA method of the present disclosure are as follows:
Heating rate: 10° C./min
Purge gas: nitrogen
Infrared Spectrum (IR) in the present disclosure were acquired by an infrared spectrometer Bruker VERTEX 70. The parameters of the Fourier Transform Infrared Spectrometry method of the present disclosure are as follows:
Laser source: mid-infrared laser source
Detector: DLATGS
Scanning times: 16
Resolution: 4.0
Interferometer: Rock-Solid™
High Performance Liquid Chromatography (HPLC) data in the present disclosure were collected from an Agilent 1260 with Diode Array Detector (DAD).
The HPLC method parameters for purity test in the present disclosure are as follows:
1. Column: Waters XBridge C18 150×4.6 mm, 5 μm
2. Mobile Phase: A: 5 mM Potassium dihydrogen phosphate+5 mM Sodium dihydrogen phosphate+0.1% Triethylamine in $H_2O$, pH=8.5
   B: Acetonitrile Gradient:

| Time (min) | % B |
|---|---|
| 0.0 | 25 |
| 30.0 | 60 |
| 35.0 | 80 |
| 37.0 | 80 |
| 37.1 | 25 |
| 42.0 | 25 |

3. Flow rate: 1.0 mL/min
4. Injection Volume: 10 μL
5. Detection wavelength: 230 nm
6. Column Temperature: 40° C.
7. Diluent: Acetonitrile: $H_2O$ (v:v)=50:50

High Performance Liquid Chromatography (HPLC) data in the present disclosure were collected from an Agilent 1260 with Diode Array Detector (DAD).

The HPLC method parameters for solubility test and dissolution tests in the present disclosure are as follows:
1. Column: Waters XBridge C18 150×4.6 mm, 5 μm
2. Mobile Phase: A: 0.1% TFA in $H_2O$
   B: 0.1% TFA in Acetonitrile
Gradient:

| Time (min) | % B |
|---|---|
| 0.0 | 8 |
| 10.0 | 50 |
| 12.0 | 90 |
| 12.1 | 8 |
| 17.0 | 8 |

3. Flow rate: 1.0 mL/min
4. Injection Volume: 10 μL
5. Detection wavelength: 230 nm
6. Column Temperature: 40° C.
7. Diluent: Acetonitrile: $H_2O$ (v:v)=50:50

According to the present disclosure, Compound I and/or its salt used as a raw material is solid (crystalline or amorphous), semisolid, wax, or oil. Preferably, compound I and/or its salt used as a raw material is a solid.

Raw materials of valbenazine free base solid used in the following examples were prepared by known methods in prior art, for example, the method disclosed in WO200805826A1. P-toluenesulfonic acid used in the following examples could be a hydrate of p-toluenesulfonic acid.

EXAMPLES

Example 1 Preparation of Form CSIII 432.1 mg of valbenazine freebase was weighed into a glass vial. 390.8 mg of p-toluenesulfonic acid was then added. 1 mL of 2-MeTHF was added into this vial and the mixture was stirred for three minutes at room temperature. 1 mL of 2-MeTHF and 200 μL of water was then added. Then the sample was stirred at −20° C. and solid was isolated to give Form CSIII. Form CSIII is a co-solvate of 2-MeTHF and $H_2O$, and the XRPD pattern is substantially as depicted in FIG. 1.

Example 2 Preparation of Form A 46.2 mg of Form CSIII was stirred in 2.3 mL of anisole at 4° C., and the solid isolated was Form N4. The XRPD pattern is substantially as depicted in FIG. 2. Form N4 was dried under vacuum at room temperature to obtain white solids. The crystalline solid obtained was confirmed to be Form A. The XRPD pattern is substantially as depicted in FIG. 3, and the XRPD data are listed in Table 1.

TABLE 1

| 2θ | d spacing | Intensity % |
|---|---|---|
| 5.88 | 15.03 | 100.00 |
| 7.06 | 12.52 | 3.97 |
| 8.68 | 10.18 | 4.82 |
| 10.98 | 8.05 | 5.50 |
| 13.29 | 6.66 | 14.80 |
| 14.27 | 6.21 | 3.81 |
| 15.75 | 5.63 | 10.38 |
| 16.26 | 5.45 | 4.06 |
| 16.96 | 5.23 | 2.53 |
| 18.15 | 4.89 | 5.91 |
| 19.00 | 4.67 | 5.70 |
| 19.76 | 4.49 | 17.66 |
| 21.58 | 4.12 | 4.90 |
| 22.88 | 3.89 | 3.61 |
| 26.98 | 3.30 | 2.41 |
| 29.40 | 3.04 | 1.21 |
| 30.00 | 2.98 | 1.14 |
| 36.01 | 2.49 | 0.31 |

Figure 4:
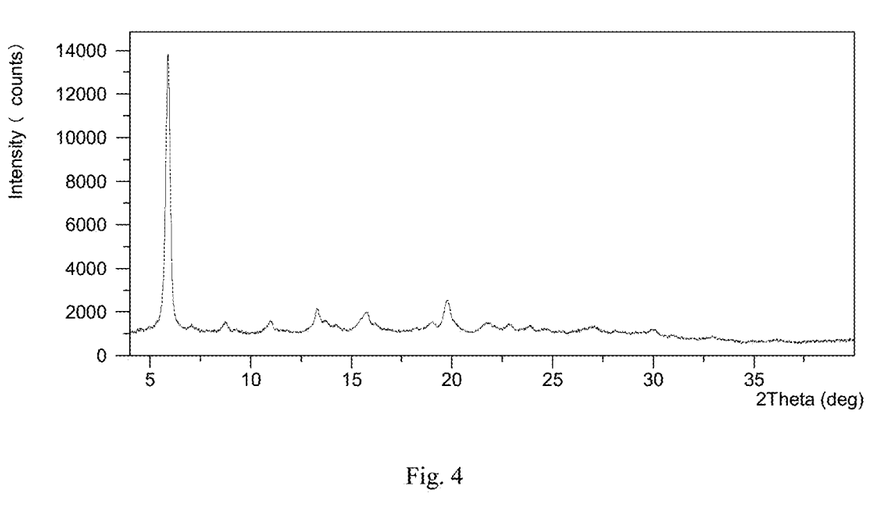
FIG. 4 shows an XRPD pattern of Form A
Figure 5:
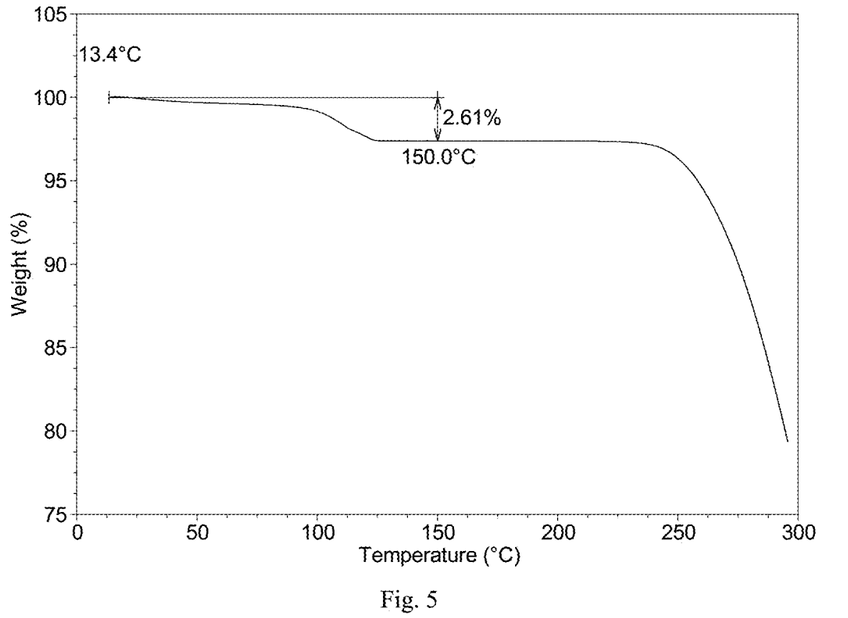
FIG. 5 shows a TGA curve of Form A
Figure 6:
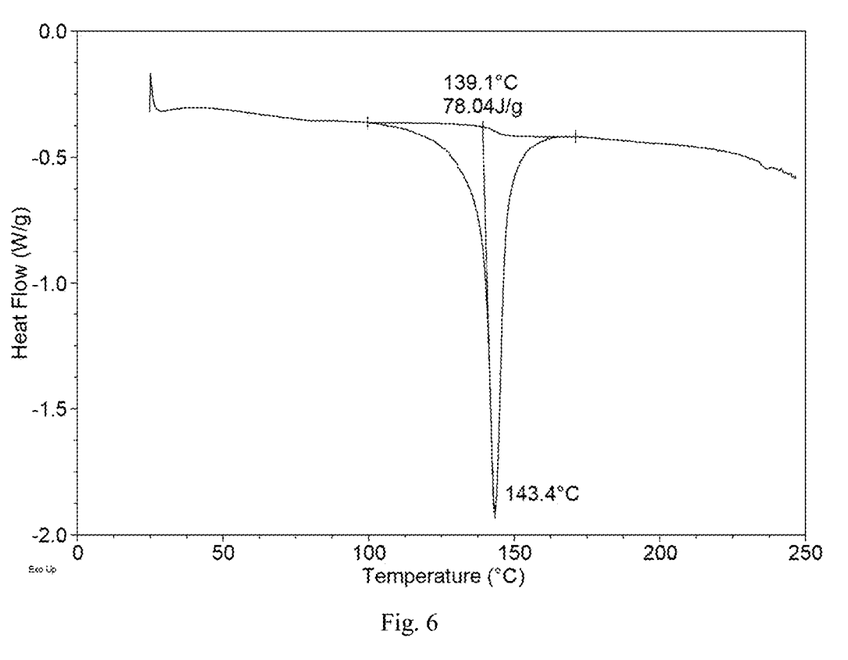
FIG. 6 shows a DSC curve of Form A

Example 3 Preparation of Form A 500.1 mg of freebase and 476.1 mg of p-toluenesulfonic acid were added into a 20-mL glass vial. 4.0 mL of 2-MeTHF was added and the mixture was stirred at −20° C. for about 1.5 hours. 6.0 mL of 2-MeTHF was added and the mixture was stirred for about 1.5 hours. After centrifuging and vacuum drying for about 1.5 hours, solid was obtained. The solid was transferred into a 100-mL glass vial and 45 mL of anisole was added. After stirring at −20° C., about 0.5 mL of Form N4 suspension was added as seeds and stirring was continued. After filtering under nitrogen protection and vacuum drying at room temperature overnight, 795.8 mg of Form A was obtained, and the solid was confirmed to be Form A (yield without counting seed: 84%). The XRPD pattern is substantially as depicted in FIG. 4, and the XRPD data are listed in Table 2. The TGA curve of Form A displayed in FIG. 5 shows about 2.61% weight loss when heated to 150° C. The DSC curve of Form A displayed in FIG. 6 shows one endothermic peak at 139.1° C., corresponding to melting endotherm.

TABLE 2

| 2θ | d spacing | Intensity % |
|---|---|---|
| 5.88 | 15.03 | 100.00 |
| 7.07 | 12.50 | 2.17 |
| 8.73 | 10.13 | 3.78 |
| 10.96 | 8.07 | 4.57 |
| 13.28 | 6.67 | 8.85 |
| 13.74 | 6.45 | 4.44 |
| 15.84 | 5.59 | 6.64 |
| 16.20 | 5.47 | 3.38 |
| 19.01 | 4.67 | 3.86 |
| 19.76 | 4.49 | 11.88 |
| 21.76 | 4.09 | 3.40 |
| 22.89 | 3.88 | 2.81 |
| 23.89 | 3.72 | 2.51 |
| 30.01 | 2.98 | 2.06 |

Example 4 IR Test of Form A

A suitable amount of Form A was used to collect infrared data. The IR spectrum is substantially as depicted in FIG. 7.

The IR spectrum shows that Form A in the present disclosure has the following absorption bands: 621.81 cm$^{-1}$ (w), 682.24 cm$^{-1}$ (s), 710.21 cm$^{-1}$ (w), 773.12 cm$^{-1}$ (w), 786.44 cm$^{-1}$ (m), 813.86 cm$^{-1}$ (w), 866.03 cm$^{-1}$ (w), 893.90 cm$^{-1}$ (w), 940.44 cm$^{-1}$ (w), 969.18 cm$^{-1}$ (w), 1011.74 cm$^{-1}$ (s), 1036.51 cm$^{-1}$ (s), 1062.25 cm$^{-1}$ (w), 1123.24 cm$^{-1}$ (s), 1192.18 cm$^{-1}$ (s), 1208.69 cm$^{-1}$ (s), 1264.51 cm$^{-1}$ (m), 1356.58 cm$^{-1}$ (w), 1385.50 cm$^{-1}$ (w), 1466.67 cm$^{-1}$ (w), 1522.01 cm$^{-1}$ (m), 1614.23 cm$^{-1}$ (w), 1748.34 cm$^{-1}$ (m) (±2 cm$^{-1}$).

Example 5 Kinetic Solubility of Form A

Simulated intestinal fluids, such as FaSSIF (fasted state simulated intestinal fluids) and FeSSIF (fed state simulated intestinal fluids) are biorelevant media. These media can better reflect the drug release affected by gastrointestinal environment. Solubility in such media is close to in vivo solubility.

20 mg of Form A in the present disclosure and 20 mg of prior art Form I were suspended in 1.5 mL of FaSSIF and 1.5 mL of FeSSIF to get saturated solutions. After equilibrium for 15 minutes, 30 minutes and 1 hour, concentrations of the saturated solutions (mg/mL) were measured by HPLC. The results are listed in Table 3.

TABLE 3

| Media | Form A | | | Prior art Form I | | |
|---|---|---|---|---|---|---|
| | 15 minutes (mg/mL) | 30 minutes (mg/mL) | 1 hour (mg/mL) | 15 minutes (mg/mL) | 30 minutes (mg/mL) | 1 hour (mg/mL) |
| FaSSIF | 31.429 | 31.306 | 31.828 | 30.637 | 30.189 | 31.010 |
| FeSSIF | 41.871 | 41.656 | 41.282 | 34.054 | 34.628 | 35.012 |

The results show that the solubility of Form A of the present disclosure is higher than that of prior art polymorph.

Example 6 Hygroscopicity of Form A

The hygroscopicity experiment was conducted according to general notice 9103 drug hygroscopicity test guidelines in 2015 edition of Chinese Pharmacopoeia. The methods are listed as follows:

1. A dry weighing bottle with a stopper (outer diameter is 50 mm and the height is 15 mm) was placed in a suitable desiccator at constant temperature of 25±1° C. (saturated solution of ammonium chloride or ammonium sulfate was placed in the lower compartment) or the a man-made climate chamber (the temperature is set as 25°±C. 1° C. and the relative humidity is 80%±2%) the day before the test. The weight is accurately weighed ($m_1$).
2. A suitable amount of the sample was spread into the weighing bottle. The thickness of the sample is generally about 1 mm, and the weight is accurately weighed ($m_2$).
3. The weighing bottle was kept open and placed under the same constant temperature and humidity mentioned above for 24 hours as well as the stopper.
4. T The stopper was put on the weighing bottle, and then the weighing bottle with stopper was accurately weighed ($m_3$).

$$\text{Percentage gain} = \frac{m_3 - m_2}{m_2 - m_1} \times 100\%$$

The hygroscopicity of Form A in the present disclosure and Form I in prior art was tested. The results are listed in Table 4.

TABLE 4

| | Form | |
|---|---|---|
| Weight (mg) | Form A | Form I in prior art |
| $m_1$ | 10340.92 | 10563.61 |
| $m_2$ | 10414.99 | 10650.56 |
| $m_3$ | 10415.17 | 10650.91 |
| Percentage gain | 0.24% | 0.40% |

According to general notice 9103 drug hygroscopicity test guidelines in 2015 edition of Chinese Pharmacopoeia, the hygroscopicity of Form A is 0.24%, while the hygroscopicity of prior art Form I is 0.40% at the same conditions. The hygroscopicity of Form A is superior to that of prior art polymorph.

Example 7 Purification Effect of Form A

Form A was prepared with free base as starting material. HPLC was applied to test the chemical purity of starting material and Form A in the present disclosure. The results are listed in Table 5.

TABLE 5

| Form | Chemical purity | Number of impurities | Purity increase |
|---|---|---|---|
| Starting material | 99.09% | 8 | — |
| Form A | 99.38% | 5 | 0.29% |

The results show that the chemical purity of Form A obtained from the starting material is improved obviously. The purity is increased from 99.09% to 99.38% and the number of impurities can be detected is reduced from 8 to 5, indicating that the Form A in the present disclosure has good purification effect.

Example 8 Stability of Form A

Four samples of Form A in the present disclosure was stored under different conditions of 25° C./60% RH in open and closed dishes for 3 months, 40° C./75% RH in closed dish for 3 months and 60° C./75% RH in closed dish for 1 week. Crystalline form and chemical impurity were checked by XRPD and HPLC, respectively. The results are shown in the table below.

TABLE 6

Figure 8:
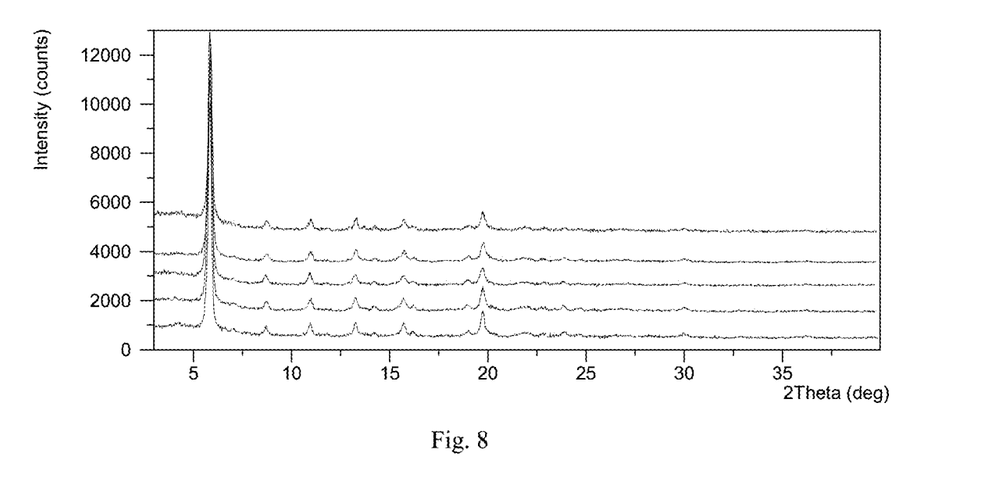
FIG. 8 shows an XRPD pattern overlay of Form A before and after stability study (from top to bottom: XRPD pattern of initial Form A, Form A after being stored under 25° C./60% RH for 3 months in open dish, Form A after being stored under 25° C./60% RH for 3 months in closed dish, Form A after being stored under 40° C./75% RH for 3 months in closed dish, Form A after being stored under 60° C./75% RH for 1 week in closed dish)

| Condition | Time | Change in solid form | Change in purity % |
|---|---|---|---|
| 25° C./60% RH (in open dish) | 3 months | No form change (FIG. 8) | 0.03 |
| 25° C./60% RH (in closed dish) | 3 months | No form change (FIG. 8) | 0 |
| 40° C./75% RH (in closed dish) | 3 months | No form change (FIG. 8) | 0.09 |
| 60° C./75% RH (in closed dish) | 1 week | No form change (FIG. 8) | 0.08 |

The results show that Form A keeps physically and chemically stable for at least 3 months at 25° C./60% RH in open dish. And Form A is physically and chemically stable for at least 3 months at 25° C./60% RH and 40° C./75% RH in closed dishes. It can be concluded that Form A has good stability under both long-term and accelerated conditions. Form A keeps stable for at least 1 week at 60° C./75% RH in closed dish, revealing that Form A has good stability under stress conditions.

Example 9 Mechanical Stability of Form A

Figure 9:
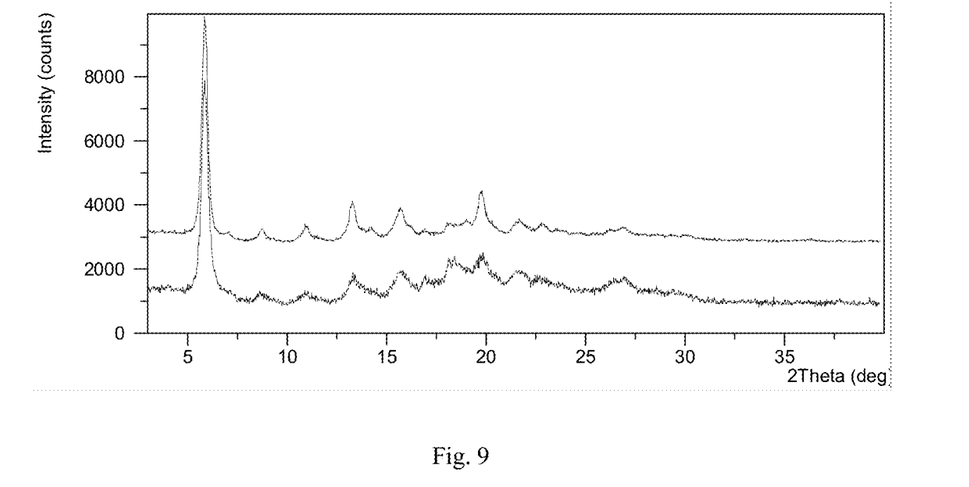
FIG. 9 shows an XRPD pattern overlay of Form A before and after tableting under 15 kN pressure (top: XRPD pattern of Form A before tableting, bottom: XRPD pattern of Form A after tableting).

About 0.1 g of Form A was added into a die, compressed at 15 kN, and held for 1 minute. And then the pressure was released and the sample in the die was taken out for XRPD test. The test results show that no form change is observed after tableting. The XRPD pattern is substantially as depicted in FIG. 9.

Example 10 Preparation of Form a Drug Product

The formulation is listed in Table 7.

TABLE 7

| No. | Component | Quantity (mg/unit) |
|---|---|---|
| 1 | Compound I ditosylate (Form A) | 73.0 |
| 2 | Mannitol (160C) | 106.0 |
| 3 | Partially pregelatinized starch (Starch 1500) | 18.0 |
| 4 | Colloidal Silicon Dioxide (AEROSIL 200 Pharma) | 1.0 |
| 5 | Magnesium stearate (5712) | 1.0 |
| Sub-total | | 199.0 |
| 6 | Magnesium stearate (5712) | 1.0 |
| Total | | 200.0 |

The preparation process is described in Table 8.

TABLE 8

| Stage | Procedure |
|---|---|
| Pre-blending | According to the formulation, weigh No. 1-5 materials into an LDPE bag and blend manually for 2 min. |
| Simulated dry granulation | Compress with a single punch tablet press (Model: ENERPAC; Die: φ 20 mm round; Weight: 500 mg; Force: 5 ± 0.5 kN). Crush the tablets with a mortar and pass the granules through a 20 mesh. |
| Final blending | Blend the extragranular excipient # 6 with granules obtained above in an LDPE bag and blend for 2 min manually. |
| Encapsulation | The lubricated blend was encapsulated with the target weight of 200 ± 2 mg using 1 # capsule shells. |
| Package | Pack each capsule in a 35 cc HDPE bottle with 1 g of desiccant inside. |

Figure 10:
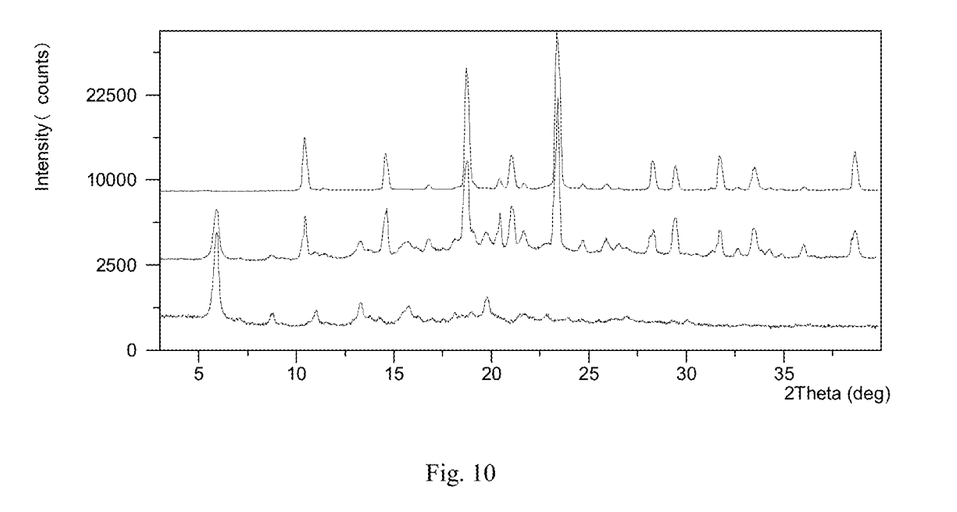
FIG. 10 shows an XRPD pattern overlay of Form A and Form A drug product (from top to bottom: XRPD pattern of excipients, Form A drug product and Form A).
Figure 11:
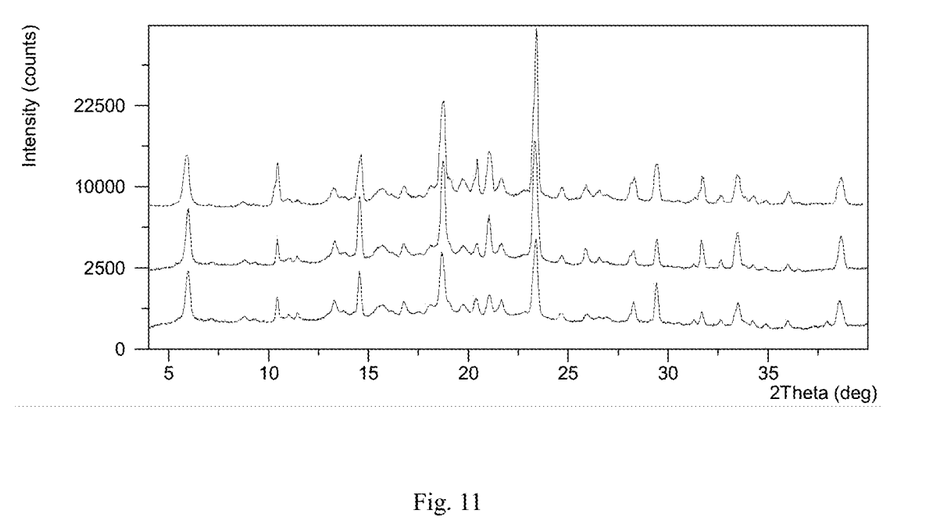
FIG. 11 shows an XRPD pattern overlay of Form A drug product before and after storage (from top to bottom: XRPD pattern of initial Form A drug product, Form A drug product after being stored under 25° C./60% RH for 3 months in closed dish, Form A drug product after being stored under 40° C./75% RH for 3 months in closed dish)

The crystalline form of Form A in capsule was tested by XRPD. The results showed that no form change was observed for Form A. Form A remained stable before and after the formulation process. The XRPD pattern is substantially as depicted in FIG. 10.

Example 11 Stability of Form A in Drug Product

The Form A capsules were packed in an HDPE and stored at 25° C./60% RH and 40° C./75% RH conditions. Crystalline form of the samples were tested to check the stability of Form A capsule at the end of 3 months. The results indicate that Form A drug product can keep stable under 25° C./60% RH and 40° C./75% RH for at least 3 months.

Example 12 Dissolution Profile of Form a Drug Product

Dissolution test was performed on Form A capsule obtained from example 10. The test conditions are as follows:
Medium: 0.1 mol/L HCl solution
Method: Paddle+Sinker
Volume: 900 mL
Speed: 50 rpm
Temperature: 37° C.

Figure 12:
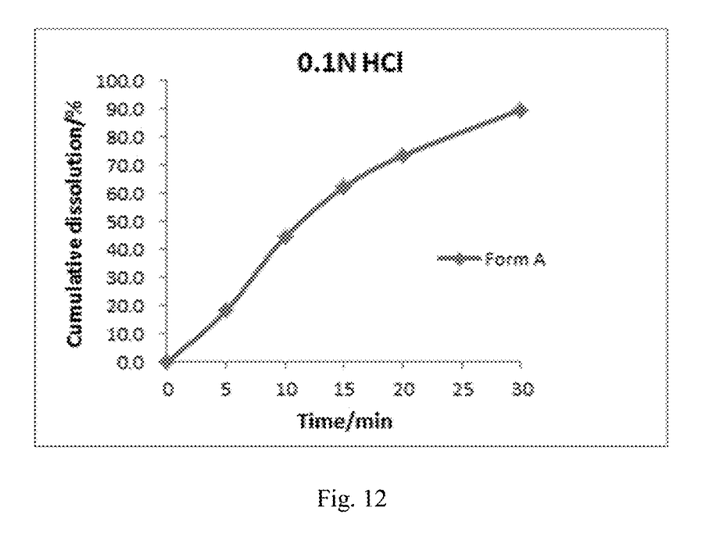
FIG. 12 shows a dissolution profile of Form A drug product

The results of dissolution study for Form A capsule are presented in Table 9 and FIG. 12. The results indicate that the dissolution of Form A capsule is more than 80% within 30 min, meeting the requirement of rapid dissolution. Form A capsule has a good dissolution.

TABLE 9

| Time (minute) | Accumulative drug release (%) |
|---|---|
| 0 | 0.0 |
| 5 | 18.2 |
| 10 | 44.5 |
| 15 | 62.2 |
| 20 | 73.4 |
| 30 | 89.7 |

Example 13 Compressibility of Form A

A manual tablet press was used for compression. A certain amount of Form A and prior art Form I were added into the dies of round tooling (Ensuring the isotropy of the tablet), compressed at suitable pressure, and then stored at room temperature for 24 h until complete elastic recovery. Hardness (H) was tested with Intelligent Tablet Hardness Tester. Diameter (D) and thickness (L) were tested with caliper. Tensile strength of the powder was calculated with the following formula: $T=2H/\pi DL$. Under a certain force, the greater the tensile strength, the better the compressibility. The recommended parameters used for the small sample quantity test are shown in the table below.

TABLE 10

The recommended parameters of tensile strength

| Dies | Amount of sample | Pressure |
|---|---|---|
| Φ6 mm round tooling | 80 mg | 10 kN |

The results of prior art Form I and Form A in the present disclosure are presented in Table 11.

TABLE 11

| Form | Thickness (mm) | Diameter (mm) | Hardness (N) | Tensile strength (MPa) |
|---|---|---|---|---|
| Form I | 2.30 | 6.04 | 16.5 | 0.86 |
| Form A | 2.33 | 6.11 | 30.4 | 1.36 |

The results indicate that the tensile strength of Form A is 1.36 MPa, while that of Form I is 0.86 MPa. Form A in the present disclosure has better compressibility than Form I.

Example 14 Flowability of Form A

Compressibility index or Carr Index is usually utilized to evaluate the flowability of powder and granules during the drug product process. Compressibility index test method is as follows: a certain amount of powder was added into a measuring cylinder and bulk volume was recorded. Then the powder was tapped to make it in the tightest state and the tapped volume was recorded. The bulk density ($\rho_0$), tapped density ($\rho_f$) were calculated and compressibility index was calculated according to c=($\rho_f$-$\rho_0$)/$\rho_f$. Criteria of flowability according to ICH Q4B Annex 13 are listed in Table 12.

TABLE 12

| Compressibility index (%) | Flowability |
|---|---|
| ≤10 | Excellent |
| 11-15 | Good |
| 16-20 | Fair |
| 21-25 | Passable |
| 26-31 | Poor |
| 32-37 | Very poor |
| >38 | Very, very poor |

Flowability evaluation results of Form A and prior art Form I are presented in Table 13, which indicate that flowability of Form A is remarkably superior to that of prior art polymorph.

TABLE 13

| Form | Bulk density (g/ml) | Tap density (g/ml) | Carr Index | Flowability |
|---|---|---|---|---|
| Form I | 0.144 | 0.174 | 17% | Fair |
| Form A | 0.179 | 0.209 | 14% | Good |

Example 15 Adhesiveness of Form A 30 mg of Form A and Form I in prior art were added into the dies of φ8 mm round tooling, compressed at 10 kN and held for 30 s. The punch was weighed and amount of material sticking to the punch was calculated. The compression was repeated several times to record the cumulative amount, maximum amount and average amount of material sticking to the punch during compression process. Detailed experimental results are summarized in Table 14.

TABLE 14

| Form | Cumulative amount (mg) | Maximum amount (mg) |
|---|---|---|
| Form I | 0.21 | 7.58 |
| Form A | 0.06 | 0.17 |

Test results indicate that maximum amount sticking to the punch of prior art Form I is more than 3 times of that of Form A. The adhesiveness of Form A is superior to that of prior art polymorph.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A valbenazine ditosylate crystalline form A, wherein the X-ray powder diffraction pattern shows characteristic peaks at 2theta values of 5.9°±0.2°, 8.7°±0.2°, 11.0°±0.2°, 13.3°±0.2°, 15.8°±0.2°, and 19.8°±0.2° using CuKα radiation.

2. A process for preparing the valbenazine ditosylate crystalline form A according to claim 1, wherein the process comprises: adding a valbenazine ditosylate solvate into an ether, stirring at −20° C.-25° C., filtering the solid, and drying to obtain the crystalline form A.

3. The process for preparing the valbenazine ditosylate crystalline form A according to claim 2, wherein said valbenazine ditosylate solvate is a 2-MeTHF and water co-solvate, said ether is anisole.

4. The process for preparing the valbenazine ditosylate crystalline form A according to claim 3, wherein said 2-MeTHF and water co-solvate is a crystalline form.

5. A pharmaceutical composition comprising a therapeutically effective amount of the valbenazine ditosylate crystalline form A according to claim 1, and a pharmaceutically acceptable carrier, a diluent or an excipient.

6. A method of treating tardive dyskinesia, comprising administering to a subject in need thereof a therapeutically effective amount of the valbenazine ditosylate crystalline form A according to claim 1.

7. The valbenazine ditosylate crystalline form A according to claim 1, wherein the valbenazine ditosylate crystalline form A is a hydrate.

* * * * *